(12) United States Patent
Rowe

(10) Patent No.: US 12,163,423 B2
(45) Date of Patent: Dec. 10, 2024

(54) RECYCLED ISOTOPE CORRECTION

(71) Applicant: Halliburton Energy Services, Inc., Houston, TX (US)

(72) Inventor: Mathew Dennis Rowe, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 18/110,241

(22) Filed: Feb. 15, 2023

(65) Prior Publication Data

US 2023/0193756 A1 Jun. 22, 2023

Related U.S. Application Data

(63) Continuation of application No. 17/487,244, filed on Sep. 28, 2021, now abandoned.

(51) Int. Cl.
*E21B 49/08* (2006.01)
*G01N 33/00* (2006.01)
*G01N 33/28* (2006.01)

(52) U.S. Cl.
CPC ........ *E21B 49/0875* (2020.05); *E21B 49/088* (2013.01); *G01N 33/0047* (2013.01); *G01N 33/2823* (2013.01)

(58) Field of Classification Search
CPC .............. E21B 49/0875; E21B 49/088; G01N 33/0047; G01N 33/2823
See application file for complete search history.

(56) References Cited

U.S. PATENT DOCUMENTS

| 3,898,837 A | 8/1975 | Boege |
| 3,899,926 A | 8/1975 | Haden |
| 4,089,207 A | 5/1978 | Patton |
| 4,635,735 A | 1/1987 | Crownover |
| 4,860,581 A | 8/1989 | Zimmerman et al. |

(Continued)

FOREIGN PATENT DOCUMENTS

| CN | 1896458 B | * 9/2012 | ............. E21B 49/00 |
| EP | 2824455 | 1/2015 | |

(Continued)

OTHER PUBLICATIONS

Michael J. Whiticar (1999). Carbon and hydrogen isotope systematics of bacterial formation and oxidation of methane., 161(1-3), 0-314.

(Continued)

*Primary Examiner* — John Fitzgerald
(74) *Attorney, Agent, or Firm* — Benjamin Ford; C. Tumey Law Group PLLC

(57) ABSTRACT

Systems and methods of the present disclosure generally relate to correcting isotope ratio calculations during wellbore operation. A method for correcting isotope ratios during a wellbore operation, comprising receiving a flow-in fluid sample from a wellbore; receiving a flow-out fluid sample from the wellbore; passing each sample to an analytical instrument operable to determine isotopes in each fluid sample; outputting a signal intensity or signal area; assigning a depth to the signal intensity or the signal area; and determining a corrected isotope ratio by subtracting a signal for the flow-in fluid sample from a signal for the flow-out fluid sample.

20 Claims, 4 Drawing Sheets

(56) References Cited

U.S. PATENT DOCUMENTS

| | | | |
|---|---|---|---|
| 4,887,464 | A | 12/1989 | Tannenbaum et al. |
| 4,936,139 | A | 6/1990 | Zimmerman et al. |
| 6,301,959 | B1 | 10/2001 | Hrametz et al. |
| 6,443,001 | B1 | 9/2002 | Duriez et al. |
| 6,585,045 | B2 | 7/2003 | Lee et al. |
| 6,609,568 | B2 | 8/2003 | Krueger et al. |
| 6,670,605 | B1 | 12/2003 | Storm, Jr. et al. |
| 6,719,049 | B2 | 4/2004 | Sherwood et al. |
| 7,032,444 | B2 | 4/2006 | Breviere et al. |
| 7,520,158 | B2 * | 4/2009 | DiFoggio ........... G01N 29/2425 73/19.1 |
| 7,529,626 | B1 | 5/2009 | Ellis |
| 8,838,390 | B1 | 9/2014 | Selman et al. |
| 9,128,076 | B2 * | 9/2015 | Lamberti ............. G01N 33/241 |
| 10,371,691 | B2 | 8/2019 | Strapoc et al. |
| 10,400,596 | B2 * | 9/2019 | Lawson ................ E21B 49/088 |
| 10,823,716 | B2 | 11/2020 | Lu |
| 11,066,929 | B2 * | 7/2021 | Lu .......................... E21B 49/02 |
| 11,313,224 | B2 | 4/2022 | Hakami et al. |
| 11,560,793 | B2 | 1/2023 | Rowe et al. |
| 11,585,743 | B2 * | 2/2023 | Rowe ................... G01N 15/088 |
| 11,796,527 | B2 * | 10/2023 | Rowe ................ G01N 33/2823 |
| 11,867,682 | B2 * | 1/2024 | Baecker ................ E21B 49/005 |
| 2004/0000433 | A1 | 1/2004 | Hill et al. |
| 2004/0014223 | A1 | 1/2004 | Audibert et al. |
| 2006/0224333 | A1 | 10/2006 | Frechin et al. |
| 2006/0249286 | A1 | 11/2006 | Drodz et al. |
| 2007/0003941 | A1 | 1/2007 | Olson et al. |
| 2008/0147326 | A1 | 6/2008 | Ellis |
| 2009/0199618 | A1 | 8/2009 | Evrard |
| 2011/0139464 | A1 | 6/2011 | Henderson et al. |
| 2013/0037707 | A1 | 2/2013 | Lamberti et al. |
| 2013/0087698 | A1 | 4/2013 | Pomerantz et al. |
| 2016/0153955 | A1 | 6/2016 | Strapoc et al. |
| 2018/0245464 | A1 | 8/2018 | Formolo |
| 2019/0368345 | A1 | 12/2019 | Rowe et al. |
| 2021/0285927 | A1 | 9/2021 | Baecker et al. |
| 2022/0065105 | A1 | 3/2022 | Rowe |
| 2022/0091090 | A1 | 3/2022 | Baecker et al. |

FOREIGN PATENT DOCUMENTS

| | | |
|---|---|---|
| EP | 2874177 | 5/2015 |
| EP | 1508794 | 5/2019 |
| KR | 10-2015-0146094 | 12/2015 |
| WO | 2004104639 | 12/2004 |
| WO | 2008017949 A1 | 2/2008 |
| WO | 2009037517 | 3/2009 |
| WO | 2015006552 | 1/2015 |

OTHER PUBLICATIONS

Lloyd M. Wenger, Robert J. Pottorf, Gordon Macleod, Glenn Otten, Sebastien Dreyfus, Holger Justwan/ExxonMobil Upstream Research Company, and Emily Sekula Wood/ University of South Carolina, Drill-Bit Metamorphism: Recognition and Impact on Show Evaluation, SPE 125218, 2009.

K. Uehara; K. Yamamoto; T. Kikugawa; N. Yoshida (2001). Isotope analysis of environmental substances by a new laser-spectroscopic method utilizing different pathlengths. , 74(1-3), 173-178.

Martin Schoell (2). (1983). Genetic Characterization of Natural Gases. AAPG Bulletin, 67.

McKinney, Daniel Eric; Flannery, Matt; Elshahawi, Hani; Stankiewicz, Artur, Clarke, Ed; Breviere, Jerome; Sharma, Sachin (). [Society of Petroleum Engineers SPE Annual Technical Conference and Exhibition—Anaheim, California, U.S.A. (Nov. 11, 2007)] SPE Annual Technical Conference and Exhibition—Advanced Mud Gas Logging in Combination with Wireline Formation Testing and Geochemical Fingerprinting for an Improved Understanding of Reservoir Architecture.

Eckhard Faber; Peter Gerling; Ingolf Dumke (1988). Gaseous hydrocarbons of unknown origin found while drilling, vol. 13, Nos. 4-6, pp. 875-879 (1988).

Berner et al., Org. Geochem., Maturity related mixing model for methane, ethane and propane, based on carbon sotopes, vol. 13, Nos. 1-3, pp. 67-72, 1988.

Bernard, Bernie B.; Brooks, James M.; Sackett, William M. (1978). Light hydrocarbons in recent Texas continental shelf and slope sediments. Journal of Geophysical Research, vol. 83 No. C8 pp. 403-4061 (1978).

European Search Report issued in European App. No. 13305982.4 dated Jan. 10, 2014.

International Search Report and Written Opinion issued in International App. No. PCT/US2014/046134 dated Nov. 6, 2014.

International Search Report and Written Opinion issued in International App. No. PCT/US2021/055848 dated Jun. 22, 2022.

Office Action Summary for U.S. Appl. No. 17/487,244 dated Feb. 1, 2023.

Office Action Summary with Form 892 for U.S. Appl. No. 17/487,244 dated Feb. 1, 2023. PDF file. 8 pages.

Geoservices. Isotope Logging Continuous isotopic ratio measurement service. Schlumberger, 2021. 21-WCMS-1065038. PDF file. 2 pages.

Halliburton. GasFact™ Gas Analysis Service. Halliburton, 2018. H08406 07/18. PDF file. 2 pages.

* cited by examiner

RECYCLED ISOTOPE CORRECTION

CROSS REFERENCE TO RELATED APPLICATIONS

This application is a continuation of U.S. patent application Ser. No. 17/487,244, filed Sep. 28, 2021, which is incorporated by reference in its entirety.

BACKGROUND

During drilling of a wellbore into a subterranean formation, formation fluid(s) may enter the wellbore and circulate with drilling fluid from the wellbore to the surface, and back into the wellbore. Determining isotopes present in the formation fluid may indicate reservoir compartmentalization and connectivity. Typically, isotopes are only measured at a wellbore flow-out location which may lead to erroneous results.

BRIEF DESCRIPTION OF THE DRAWINGS

These drawings illustrate certain aspects of some examples of the present invention and should not be used to limit or define the invention.

DETAILED DESCRIPTION

Systems and methods of the present disclosure generally relate to wellbore operations and, more particularly, may relate to correcting isotope ratio calculations during wellbore operations.

In particular examples, a lag equation may be employed to account for depth at which isotopes are removed from the formation. In certain examples, a sampling device may continuously extract a fluid sample at a flow-in location for a wellbore such as at a suction line, for example. A second sampling device may continuously extract a fluid sample at a flow-out location for the wellbore such as at a flow line, for example. Each of the sampling devices may extract sample fluids from drilling fluid in the form of a gas sample and/or a liquid sample. A flow-in sample and a flow-out sample may each be sent to a sample conditioner, and pressure and flow controller. Each sample may then flow to an analytical instrument(s) that may analyze the concentration of carbon-12 and carbon-13.

In particular examples, the analytical instruments may include a cavity ring-down spectrometer, an isotopic ratio mass spectrometer, a laser dispersion spectrometer, or other suitable devices that are able to analyze carbon isotopes. A signal intensity (e.g., a height of the signal) or area (e.g., area underneath the curve) outputted from these instruments may be recorded. The signal intensity or the area may be assigned a depth based on a lag equation. The signal from the flow-in sample may be subtracted from the signal from the flow-out sample, with or without a correction/calibration factor, to provide a corrected isotope ratio. For example, isotope analysis may be performed with a single instrument and the signals may be directly subtracted. In other examples, the isotope analysis may be performed on separate instruments, and the correction factor may be used to account for instrument bias.

The same methodology may also be performed for hydrogen, nitrogen, oxygen, sulfur, and/or other isotopes. In some examples, a physical separation device may be disposed upstream to the analytical instrument(s) to separate molecules based on species, molecular size, and/or functional groups. The samples may also be oxidized before isotope analysis to simplify the analysis.

Figure 1:
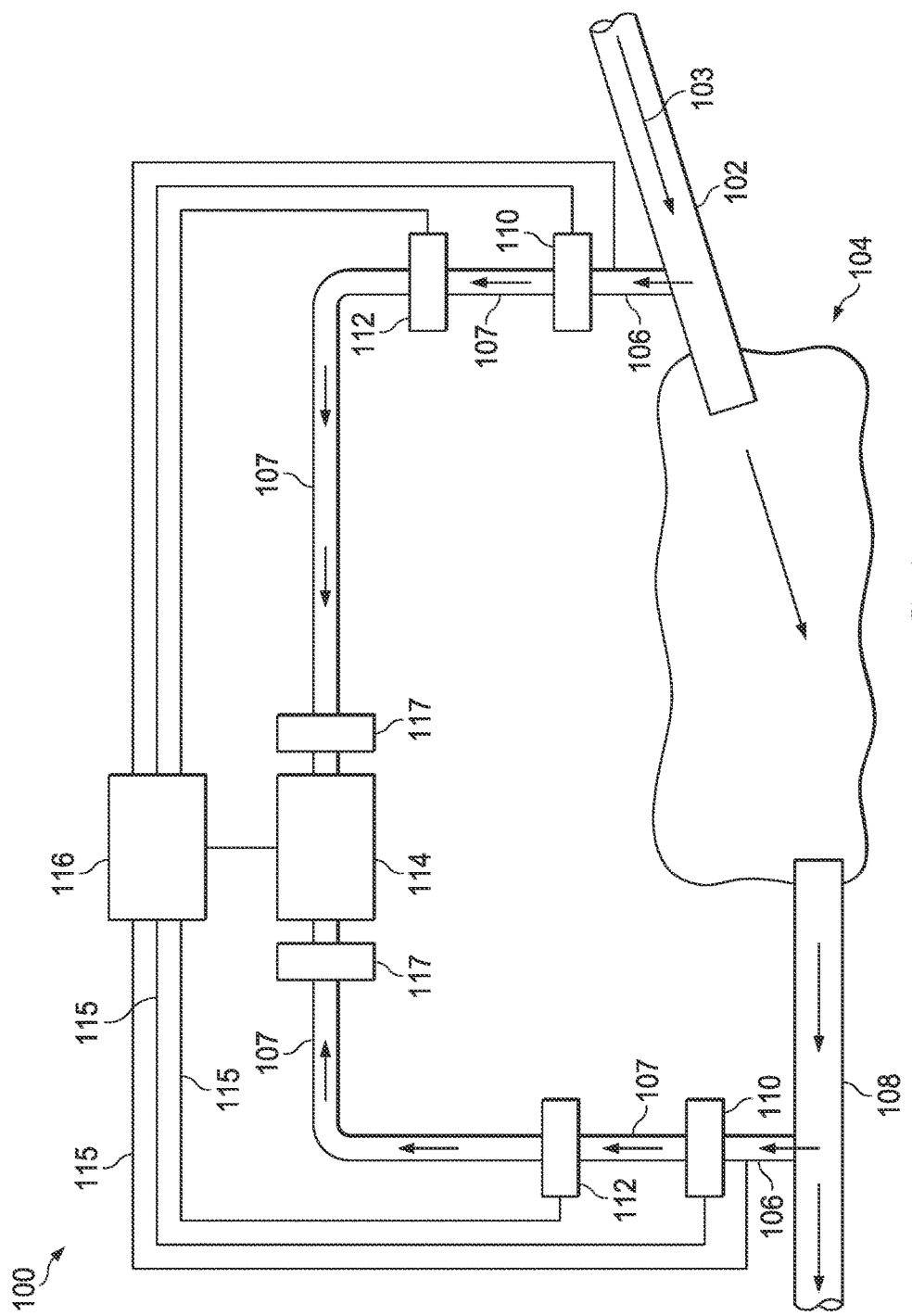
FIG. 1 illustrates a system with a single analytical instrument for correcting isotope ratio calculations, in accordance with particular examples of the present disclosure.

FIG. 1 illustrates a system 100 for correcting isotope ratio calculations, in accordance with examples of the present disclosure. A flow line 102 may pass fluid 103 directly from a wellbore into a mud pit 104. A first sampling device 106 may be in fluid communication with the flow line 102. The first sampling device 106 may receive a sample of the fluid 103 from the flow line 102. A second sampling device 106 may be disposed at a suction line 108 and may also receive a sample of the fluid 103 that passes through the suction line 108 from the mud pit 104.

The sampling devices 106 may each include any suitable sampling device for continuously receiving a fluid sample directly from the flow line 102 and the suction line 108, such as, for example, Quantitative Gas Measurement Extractor, Constant Volume Extractor, Constant Volume and Temperature Extractor. Each sample may pass via conduits 107 to a sample conditioner 110, a pressure and flow controller 112, and then to an analytical instrument 114. The sample conditioner 110 may include a condensate removal jar, coalescing filter, sample dryer, and/or membrane filter.

Figure 2:
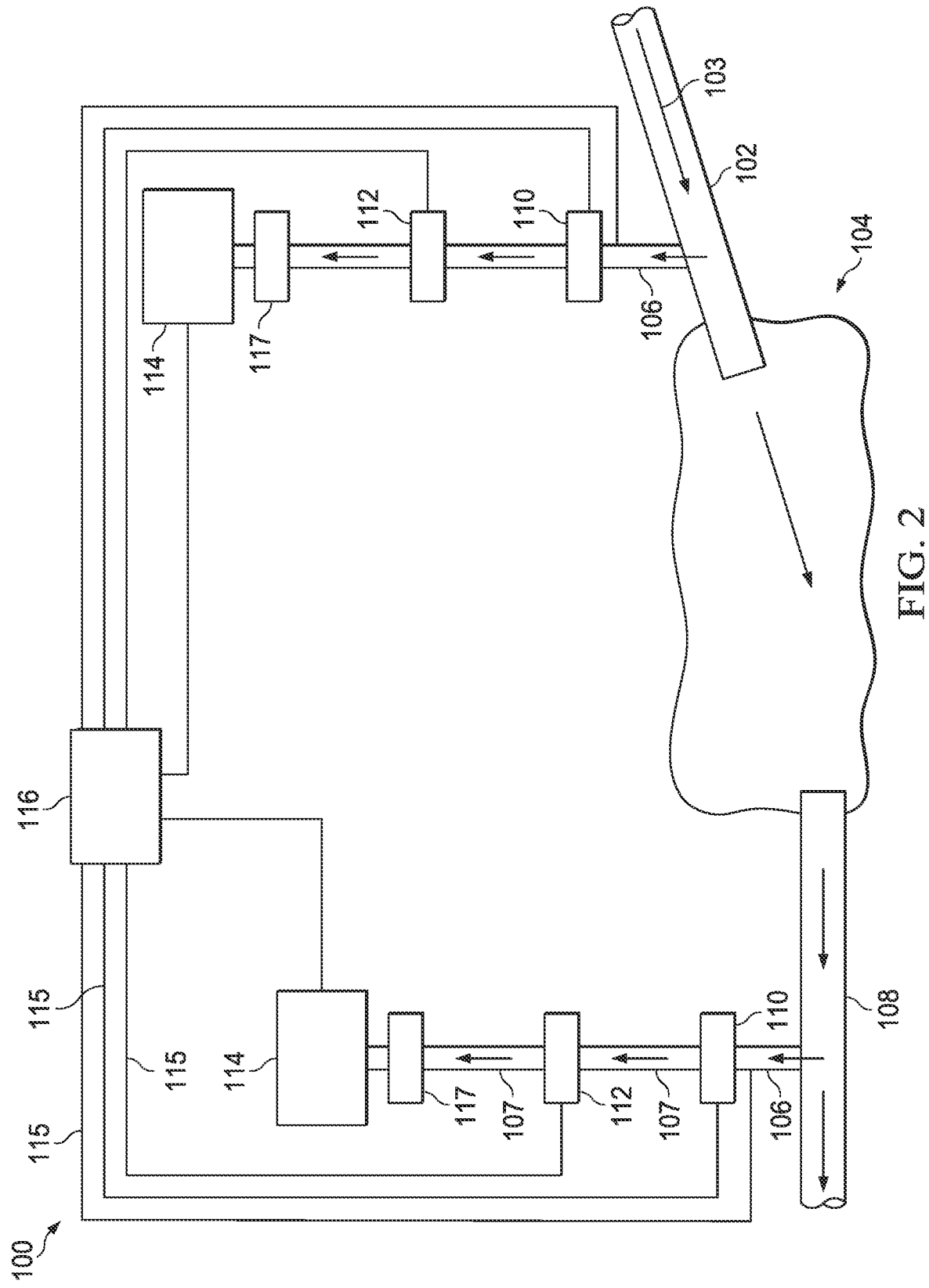
FIG. 2 illustrates a system with multiple analytical instruments for correcting isotope ratio calculations, in accordance with particular examples of the present disclosure.

With additional reference to FIG. 2, in some examples, the system 100 may further include a second analytical instrument 114. It should be noted that when using separate analytical instruments, the isotope analysis a correction factor may be used to account for instrument bias (e.g., Equation 2).

The analytical instruments 114 may include a cavity ring-down spectrometer, an isotopic ratio mass spectrometer, a laser dispersion spectrometer, or other suitable devices that analyze (e.g., determine) carbon isotopes.

The sampling devices 106, the sample conditioner 110, the pressure and flow controller 112, and the analytical instrument 114 may be in communication (e.g., wired or wireless communication paths 115) with a computer 116 that may process data from sampling devices 106, the sample conditioner 110, the pressure and flow controller 112, and the analytical instrument 114.

In some examples, a physical separation device 117 may be disposed upstream to the analytical instrument(s) to separate molecules based on molecular size or functional groups The separation device 117 may include a gas chromatography column. The samples may also be oxidized before isotope analysis to simplify the analysis. The samples may be oxidized with a flame or a furnace with a catalyst.

The computer 116 may operate the system 100 and may include any instrumentality or aggregate of instrumentalities operable to compute, estimate, classify, process, transmit, receive, retrieve, originate, switch, store, display, manifest, detect, record, reproduce, handle, or utilize any form of information, intelligence, or data for business, scientific, control, or other purposes. The computer 116 may be any processor-driven device, such as, but not limited to, a personal computer, laptop computer, smartphone, tablet, handheld computer, dedicated processing device, and/or an array of computing devices. In addition to having a processor, the computer 116 may include a server, a memory, input/output ("I/O") interface(s), and a network interface. The memory may be any computer-readable medium, coupled to the processor, such as RAM, ROM, and/or a removable storage device for storing data and a database management system ("DBMS") to facilitate management of data stored in memory and/or stored in separate databases. The computer 116 may also include display devices such as a monitor featuring an operating system, media browser, and the ability to run one or more software applications. Additionally, the computer 116 may include non-transitory computer-readable media. Non-transitory computer-readable media may include any instrumentality or aggregation of instrumentalities that may retain data and/or instructions for a period of time.

The computer 116 may utilize lag equations to determine a corrected isotope ratio. A signal intensity (e.g., a height of the signal) or area (e.g., area underneath the curve) outputted from the instruments 114 may be recorded by the computer 116. The signal intensity or the area may be assigned a depth based on a lag equation. The signal from the flow-in sample may be subtracted from the signal from the flow-out sample, with or without a correction/calibration factor, to provide a corrected isotope ratio. For example, isotope analysis may be performed with a single instrument and the signals may be directly subtracted. In other examples, the isotope analysis may be performed on separate instruments, and the correction factor may be used to account for instrument bias.

A first lag equation for usage of separate analytical instruments may be defined by Equation (1):

$$\text{corrected isotope ratio} = \left(\frac{\frac{^{13}C}{^{12}C}Sample}{\frac{^{13}C}{^{12}C}Standard\text{-}Constant} - 1\right) * 1000 =$$

$$\left(\frac{\frac{Signal^{13}C * Calibration\ Factor}{Signal^{12}C * Calibration\ Factor}Sample}{\frac{^{13}C}{^{12}C}Standard\text{-}Constant} - 1\right) * 1000 =$$

$$\left(\frac{\frac{Signal^{13}C_{Out} * Calibration\ Factor_{Out} - Signal^{13}C_{In} * Calibration\ Factor_{In}}{Signal^{12}C_{Out} * Calibration\ Factor_{Out} - Signal^{12}C_{In} * Calibration\ Factor_{In_{Sample}}}}{\frac{^{13}C}{^{12}C}Standard\text{-}Constant} - 1\right) * 1000$$

where $^{13}C$ is carbon-13; $^{12}C$ is a sample of carbon-12; $^{12}C_{Standard\text{-}Constant}$ is a constant value; Signal $^{13}C$ is a measured signal for carbon-13; Signal $^{12}C$ is a measured signal for carbon-12; Signal $^{12}C_{In}$ is the measured signal for the carbon-12 at the flow line 102; Signal $^{12}C_{Out}$ is the measured signal for the carbon-12 at the suction line 108; Signal $^{13}C_{In}$ is the measured signal for carbon-13 at the flow line 102, Signal $^{13}C_{Out}$ is the measured signal for the carbon-13 at the suction line 108; the Signal may be area (e.g., area under curve of signal) or intensity (e.g., height of signal); the Calibration Factor may be a constant value or an equation. For example, the isotope analysis may be performed on separate instruments (e.g., instruments 114 on FIG. 2), and the Calibration Factor may be used to account for instrument bias.

A second lag equation for a single analytical instrument without the Calibration Factor may be defined by:

$$\text{corrected isotope ratio} = \left(\frac{\frac{^{13}C}{^{12}C}Sample}{\frac{^{13}C}{^{12}C}Standard\text{-}Constant} - 1\right) * 1000 = \quad \text{Eq. (2)}$$

$$\left(\frac{\frac{Signal^{13}C}{Signal^{12}C}Sample}{\frac{^{13}C}{^{12}C}Standard\text{-}Constant} - 1\right) * 1000 =$$

$$\left(\frac{\frac{Signal^{13}C_{Out} - Signal^{13}C_{In}}{Signal^{12}C_{Out} - Signal^{12}C_{In}}Sample}{\frac{^{13}C}{^{12}C}Standard\text{-}Constant} - 1\right) * 1000$$

where $^{13}C$ is carbon-13; $^{12}C$ is a sample of carbon-12; $^{12}C_{Standard\text{-}Constant}$ is a constant value; Signal $^{13}C$ is a measured signal for carbon-13; Signal $^{12}C$ is a measured signal for carbon-12; Signal $^{12}C_{In}$ is the measured signal for the carbon-12 at the flow line 102; Signal $^{12}C_{Out}$ is the measured signal for the carbon-12 at the suction line 108; Signal $^{13}C_{In}$ is the measured signal for carbon-13 at the flow line 102, Signal $^{13}C_{Out}$ is the measured signal for the carbon-13 at the suction line 108; the Signal may be area (e.g., area under curve of signal) or intensity (e.g., height of signal).

Figure 3:
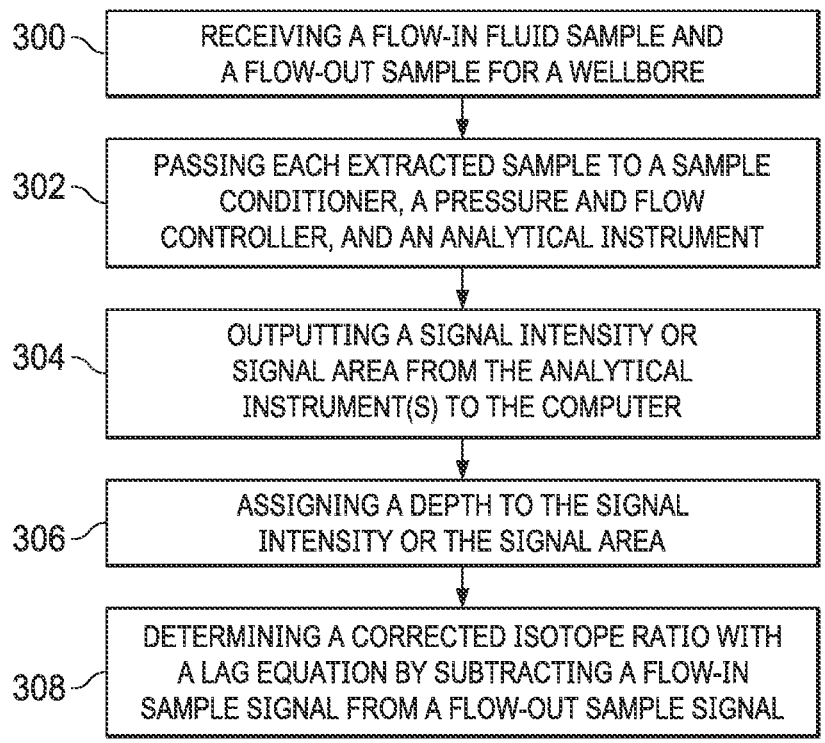
FIG. 3 illustrates an exemplary method to determine a corrected isotope ratio during wellbore operations, in accordance with particular examples of the present disclosure.

FIG. 3 illustrates an exemplary method to determine a corrected isotope ratio during wellbore operations, in accordance with particular examples of the present disclosure. At step 300, a flow-in fluid sample and a flow-out fluid sample may be extracted from a flow line and a suction line for a wellbore, respectively, as shown on FIGS. 1 and 2, for example. The extraction of fluid samples may occur continuously with the sampling devices. The fluid samples may include gas and/or liquid.

At step 302, each extracted sample may be extracted with a sampling device and pass through a sample conditioner, a pressure and flow controller, and analytical instrument for analysis with a computer, as shown on FIGS. 1 and 2, for example. The analytical instrument(s) may include a cavity ring-down spectrometer, an isotopic ratio mass spectrometer, a laser dispersion spectrometer, or other suitable devices that are able to analyze/determine carbon isotopes.

At step 304, the signal intensity (e.g., a height of the signal) or area (e.g., area underneath the curve) may be outputted from the analytical instrument(s) to the computer for recordation. At step 306, the signal intensity or the area may be assigned a depth. At step 308, the computer may determine a corrected isotope ratio with Equation 1 or Equation 2. For example, the signal from the flow-in sample may be subtracted from the signal from the flow-out sample, with or without a correction/calibration factor, to provide a corrected isotope ratio.

Figure 4:
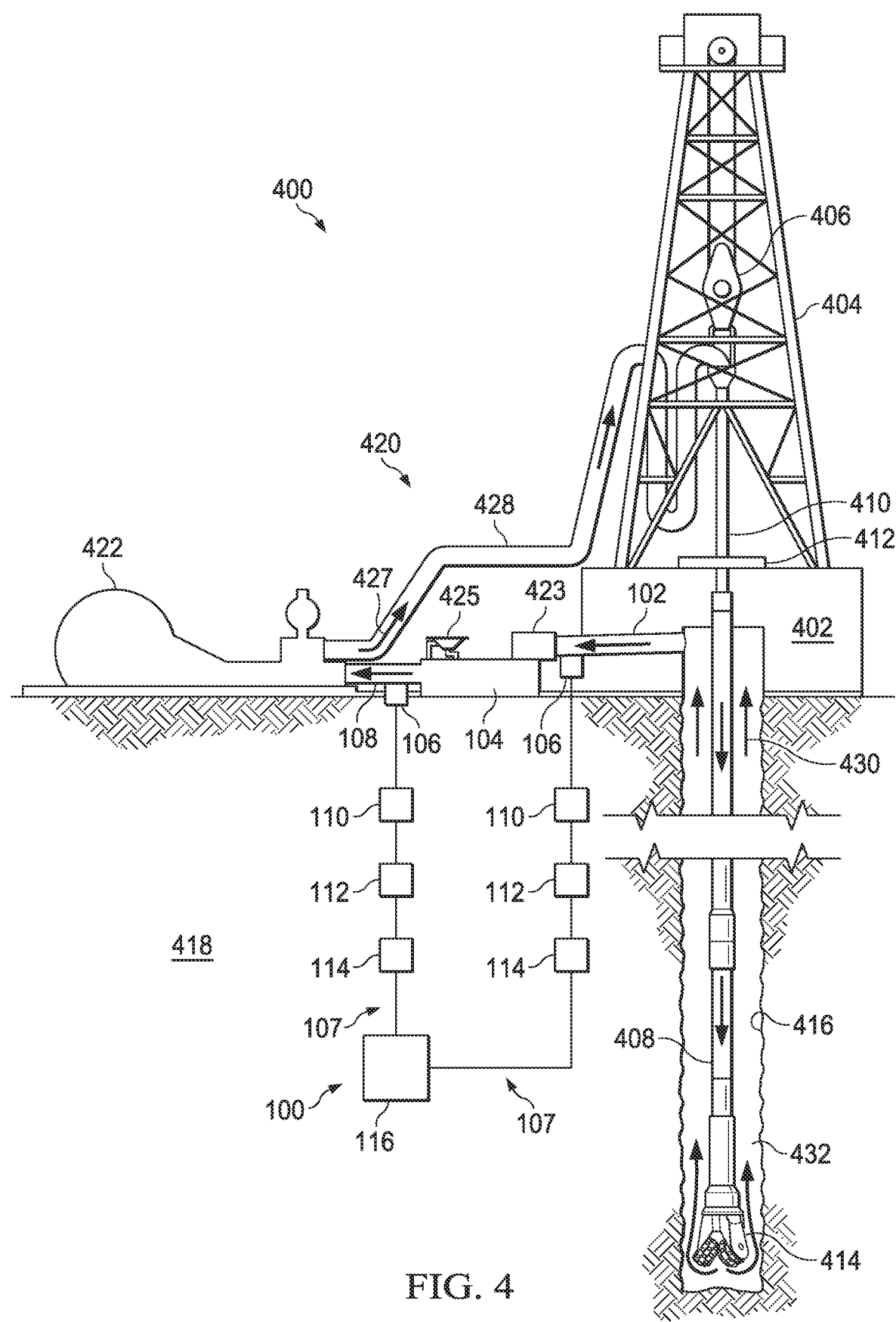
FIG. 4 is a schematic diagram of an exemplary drilling system including the system for correcting isotope ratio calculations, in accordance with particular examples of the present disclosure.

FIG. 4 illustrates a drilling system 400 including the system 100 and the workflow of FIG. 3 in accordance with particular examples of the present disclosure. It should be noted that while FIG. 4 depicts a land-based drilling system, those skilled in the art will readily recognize that the principles described herein are equally applicable to subsea drilling operations that employ floating or sea-based platforms and/or rigs, without departing from the scope of the present disclosure.

As illustrated, the drilling system 400 may include a drilling platform 402 that supports a derrick 404 having a traveling block 406 for raising and lowering a drill string 408. The drill string 408 may include, but is not limited to, drill pipe and coiled tubing, as generally known to those skilled in the art. A top drive or kelly 410 may support the drill string 408. The drill string 408 may be lowered through a rotary table 412, in some examples. A drill bit 414 may be attached to the distal end of the drill string 408 and may be driven either by a downhole motor and/or via rotation of the drill string 408 from the well surface. Without limitation, the drill bit 414 may include, roller cone bits, PDC bits, natural diamond bits, any hole openers, reamers, coring bits, and the like. As the drill bit 414 rotates, it may create a wellbore 416 that penetrates a subterranean formation 418.

The drilling system 400 may further include a fluid monitoring and handling system 420 comprising component parts such as a mud pump 422, a solids control device 423, a mixing hopper 425 and the mud pit 104. The mud pump 422 may include any conduits, pipelines, trucks, tubulars, and/or pipes used to convey clean drilling fluid 427 downhole. The mud pump 422 may also include any pumps, compressors, or motors (e.g., surface or downhole) used to move the clean drilling fluid 427, as well as any valves or related joints used to regulate the pressure or flowrate of the clean drilling fluid 427, and any sensors (e.g., pressure, temperature, flow rate), gauges, or combinations thereof, for example. The mud pump 422 may circulate the clean drilling fluid 427 from the mud pit 104 via the suction line 108.

The mud pump 422 may circulate the clean drilling fluid 427 through a feed pipe 428 and to the top drive or kelly 410, which may convey the clean drilling fluid 427 downhole through the interior of the drill string 408 and through one or more orifices in the drill bit 414. The now circulated drilling fluid 430 may then be circulated back to the surface via an annulus 432 defined between the drill string 408 and the walls of the wellbore 416. At the surface, the circulated drilling fluid 430 may be conveyed to the solids control device 423 via the flow line 102. The solids control device 423 may include one or more of a shaker (e.g., shale shaker), a centrifuge, a hydro-cyclone, a separator (including magnetic and electrical separators), a de-silter, a de-sander, a separator, a filter (e.g., diatomaceous earth filters), a heat exchanger, and any fluid reclamation equipment. The solids control device 423 may remove and separate recovered solids from the circulated drilling fluid 430. After passing through the solids control device 423, the clean drilling fluid 427 may move into the mud pit 104.

The sampling device(s) 106 may continuously sample/receive fluid samples. The fluid samples may pass through the sample conditioner 110, the pressure and flow controller 112, and the analytical instrument 114. As noted previously, the analytical instruments 114 may include a cavity ring-down spectrometer, an isotopic ratio mass spectrometer, a laser dispersion spectrometer, or other suitable devices that analyze carbon isotopes. The computer 116 may receive isotope information from the analytical instrument(s) 114 and may utilize a lag equation (e.g., Equation 1 or Equation 2) to determine a corrected isotope ratio. For example, the signal intensity (e.g., a height of the signal) or area (e.g., area underneath the curve) outputted from the instruments 114 may be recorded by the computer 116. The signal intensity or the area may be assigned a depth based on the lag equation. The signal from the flow-in sample may be subtracted from the signal from the flow-out sample, with or without a correction/calibration factor, to provide a corrected isotope ratio.

For example, isotope analysis may be performed with a single instrument and the signals may be directly subtracted. In other examples, the isotope analysis may be performed on separate instruments, and the correction factor may be used to account for instrument bias. The same methodology may also be performed for hydrogen, nitrogen, oxygen, sulfur, and/or other isotopes.

Accordingly, the systems and methods of the present disclosure may utilize lag equations to provide a corrected isotope ratio. The systems and methods may include any of the various features disclosed herein, including one or more of the following statements.

Statement 1. A method for correcting isotope ratios during a wellbore operation, comprising: receiving a flow-in fluid sample from a wellbore; receiving a flow-out fluid sample from the wellbore; passing each sample to an analytical instrument operable to determine isotopes in each fluid sample; outputting a signal intensity or signal area; assigning a depth to the signal intensity or the signal area; and determining a corrected isotope ratio by subtracting a signal for the flow-in fluid sample from a signal for the flow-out fluid sample.

Statement 2. The method of the statement 1, further comprising passing each sample through a sample conditioner.

Statement 3. The method of the statement 2, further comprising passing each sample through a flow and pressure controller.

Statement 4. The method of any of the preceding statements, further comprising passing each sample through a separation device to separate species within each sample.

Statement 5. The method of any of the preceding statements, further comprising receiving the flow-in fluid sample from a flow line of a drilling system.

Statement 6. The method of any of the preceding statements, further comprising receiving the flow-out fluid sample from a suction line of a drilling system.

Statement 7. The method of any of the preceding statements, further comprising passing each sample to separate analytical instruments operable to determine the isotopes in each fluid sample.

Statement 8. The method of any of the preceding statements, further comprising implementing a correction factor to determine the corrected isotope ratio due to analytical instrument bias.

Statement 9. The method of any of the preceding statements, further comprising continuously sampling the flow-in fluid sample.

Statement 10. The method of any of the preceding statements, further comprising continuously sampling the flow-out fluid sample.

Statement 11. A system for correcting isotope ratios during a wellbore operation, comprising: an analytical instrument operable to determine isotopes in a wellbore fluid; a first fluid sampling device disposed at a flow-in location for a wellbore; a second fluid sampling device disposed at a flow-out location for the wellbore; and a computer operable to: receive a signal intensity or signal area from the analytical instrument; assign a depth to the signal intensity or the signal area; and determine a corrected isotope ratio by subtracting a signal for a flow-in fluid sample from a signal for the flow-out fluid sample.

Statement 12. The system of any of the statements 11, further comprising a flow and pressure controller disposed upstream to the analytical instrument.

Statement 13. The system of the statement 11 or the statement 12, further comprising a sample conditioner disposed upstream to the analytical instrument.

Statement 14. The system of any of the statements 11-13, further comprising a separation device operable to separate species within each sample.

Statement 15. The system of any of the statements 11-14, further comprising a second analytical instrument operable to determine the isotopes in the wellbore fluid.

Statement 16. The system of any of the statements 11-15, wherein the computer is further operable to implement a correction factor to determine the corrected isotope ratio due to analytical instrument bias.

Statement 17. The system of any of the statements 11-16, wherein the second sampling device is disposed at a suction line of a drilling system.

Statement 18. The system of any of the statements 11-17, wherein the first sampling device is disposed at a flow line of a drilling system.

Statement 19. The system of any of the statements 11-18, wherein the first sampling device is operable to continuously sample the wellbore fluid.

Statement 20. The system of any of the statements 11-19, wherein the second sampling device is operable to continuously sample the wellbore fluid.

The preceding description provides various examples of the systems and methods of use disclosed herein which may contain different method steps and alternative combinations of components. It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method for correcting isotope ratios during a wellbore operation, comprising:
    passing a first fluid sample from a wellbore through a first analytical instrument and to a mud pit;
    measuring an isotope ratio of the first fluid sample with the first analytical instrument;
    passing a second fluid sample from the mud pit through a second analytical instrument;
    measuring an isotope ratio of the second fluid sample with the second analytical instrument; and
    determining a corrected isotope ratio with a lag equation and the isotope ratios measured by the analytical instruments.

2. The method of claim 1, further comprising passing each sample through a sample conditioner.

3. The method of claim 1, further comprising passing each sample through a flow and pressure controller.

4. The method of claim 1, further comprising passing each sample through a separation device to separate species within each sample.

5. The method of claim 1, further comprising receiving the first fluid sample from a flow line of a drilling system.

6. The method of claim 1, further comprising receiving the second fluid sample from a suction line of a drilling system.

7. The method of claim 1, wherein the first analytical instrument and the second analytical instrument are positioned on opposing ends of the mud pit.

8. The method of claim 1, further comprising drilling the wellbore while determining the corrected isotope ratio.

9. The method of claim 1, wherein the mud pit is adjacent to the analytical instruments.

10. The method of claim 9, further comprising implementing a correction factor to determine the corrected isotope ratio due to analytical instrument bias.

11. A system for correcting isotope ratios during a wellbore operation, comprising:
    an analytical instrument operable to measure isotopes in a wellbore fluid;
    a first fluid sampling device positioned to recover a first fluid sample from a wellbore;
    a second fluid sampling device positioned to recover a second fluid sample from the wellbore, wherein the sampling devices are in communication with the analytical instrument; and
    a computer in communication with the analytical instrument, the computer operable to:
        receive an isotope ratio of the first fluid sample from the analytical instrument;

receive an isotope ratio of the second fluid sample from the analytical instrument; and determine a corrected isotope ratio with a lag equation and the isotope ratios.

12. The system of claim 11, further comprising a flow and pressure controller disposed upstream to the analytical instrument.

13. The system of claim 11, further comprising a sample conditioner disposed upstream to the analytical instrument.

14. The system of claim 11, further comprising a separation device operable to separate species within each sample.

15. The system of claim 11, wherein the second fluid sampling device is disposed at a suction line of a drilling system.

16. The system of claim 11, wherein the first fluid sampling device is disposed at a flow line of a drilling system.

17. The system of claim 11, wherein the first fluid sampling device is adjacent to a mud pit.

18. The system of claim 17, wherein the second fluid sampling device is positioned on an end of the mud pit opposite to the first fluid sampling device.

19. The system of claim 11, further comprising a second analytical instrument operable to determine the isotopes in the wellbore fluid.

20. The system of claim 19, wherein the computer is further operable to implement a correction factor to determine the corrected isotope ratio due to analytical instrument bias.

* * * * *